United States Patent
Schmitz, Sr. et al.

(10) Patent No.: US 9,096,853 B2
(45) Date of Patent: Aug. 4, 2015

(54) MODIFIED SIRNA MOLECULES INCORPORATING 5-FLUORO-2'-DEOXYURIDINE RESIDUES TO ENHANCE CYTOTOXICITY

(71) Applicants: John C. Schmitz, Sr., Pittsburgh, PA (US); Edward Chu, Pittsburgh, PA (US); William H. Gmeiner, Yadkinville, NC (US)

(72) Inventors: John C. Schmitz, Sr., Pittsburgh, PA (US); Edward Chu, Pittsburgh, PA (US); William H. Gmeiner, Yadkinville, NC (US)

(73) Assignees: U.S. Department of Veterans Affairs, Washington, DC (US); University of Pittsburgh-Of the Commonwealth System of Higher Education, Pittsburgh, PA (US); Wake Forest University Health Sciences, Winston-Salem, NC (US)

( * ) Notice: Subject to any disclaimer, the term of this patent is extended or adjusted under 35 U.S.C. 154(b) by 0 days.

(21) Appl. No.: 14/030,327

(22) Filed: Sep. 18, 2013

(65) Prior Publication Data
US 2014/0088300 A1    Mar. 27, 2014

Related U.S. Application Data

(60) Provisional application No. 61/704,685, filed on Sep. 24, 2012.

(51) Int. Cl.
C07H 21/02    (2006.01)
C12N 15/113    (2010.01)
C12N 15/11    (2006.01)

(52) U.S. Cl.
CPC ............ *C12N 15/113* (2013.01); *C12N 15/111* (2013.01); *C12N 15/1137* (2013.01); *C12N 2310/14* (2013.01); *C12N 2310/344* (2013.01)

(58) Field of Classification Search
None
See application file for complete search history.

(56) References Cited

U.S. PATENT DOCUMENTS

| | | | | |
|---|---|---|---|---|
| 5,663,321 | A * | 9/1997 | Gmeiner et al. | 536/25.5 |
| 2003/0143732 | A1* | 7/2003 | Fosnaugh et al. | 435/325 |
| 2004/0018176 | A1* | 1/2004 | Tolentino et al. | 424/93.21 |
| 2009/0208564 | A1* | 8/2009 | Li et al. | 424/450 |

OTHER PUBLICATIONS

Schmitz et al (Cancer Res 2004;64:1431-1435).*
Burnett, J.C. and Rossi, J.J. (2012) RNA-based therapeutics: current progress and future prospects. *Chemistry & Biology*, 19, 60-71.
DeVincenzo, J., Lambkin-Williams, R., Wilkinson, T., Cehelsky, J., Nochur, S., Walsh, E., Meyers, R., Gollob, J. and Vaishnaw, A. (2010) A randomized, double-blind, placebo-controlled study of an RNAi-based therapy directed against respiratory syncytial virus. *Proc Natl Acad Sci*, 107, 8800-8805.
Elbashir, S.M., Harborth, J., Lendeckel, W., Yalcin, A., Weber, K. and Tuschl, T. (2001) Duplexes of 21-nucleotide RNAs mediate RNA interference in cultured mammalian cells. *Nature*, 411, 494-498.
Chiu, Y.L. and Rana, T.M. (2003) siRNA function in RNAi: a chemical modification analysis. *RNA*, 9, 1034-1048.
Elbashir, S.M., Martinez, J., Patkaniowska, A., Lendeckel, W. and Tuschl, T. (2001) Functional anatomy of siRNAs for mediating efficient RNAi in Drosophila melanogaster embryo lysate. *The EMBO J*, 20, 6877-6888.
Watts, J.K., Deleavey, G.F. and Damha, M.J. (2008) Chemically modified siRNA: tools and applications. *Drug Discovery Today*, 13, 842-855
Jackson, A.L., Burchard, J., Leake, D., Reynolds, A., Schelter, J., Guo, J., Johnson, J.M., Lim, L., Karpilow, J., Nichols, K. et al. (2006) Position-specific chemical modification of siRNAs reduces "off-target" transcript silencing. *RNA*, 12, 1197-1205.
Judge, A.D., Bola, G., Lee, A.C. and MacLachlan, I. (2006) Design of noninflammatory synthetic siRNA mediating potent gene silencing in vivo. *Molecular Therapy : J of the American Society of Gene Therapy*, 13, 494-505.
Cihlar, T. and Ray, A.S. (2010) Nucleoside and nucleotide HIV reverse transcriptase inhibitors: 25 years after zidovudine. *Antiviral Res.*, 85, 39-58.
Sampath, D., Rao, V.A. and Plunkett, W. (2003) Mechanisms of apoptosis induction by nucleoside analogs. *Oncogene*, 22, 9063-9074.
Schmitz, J.C., Chen, T.M. and Chu, E. (2004) Small interfering double-stranded RNAs as therapeutic molecules to restore chemosensitivity to thymidylate synthase inhibitor compounds. *Cancer Res*, 64, 1431-1435.
Carreras, C.W. and Santi, D.V. (1995) The catalytic mechanism and structure of thymidylate synthase. *Annual Review of biochemistry*, 64, 721-762.
Danenberg, P.V. (1977) Thymidylate synthetase—a target enzyme in cancer chemotherapy. *Biochimica et Biophysica Acta*, 473, 73-92.
Shoichet, B.K., Stroud, R.M., Santi, D.V., Kuntz, I.D. and Perry, K.M. (1993) Structure-based discovery of inhibitors of thymidylate synthase. *Science*, 259, 1445-1450.
Smith, S.G., Lehman, N.L. and Moran, R.G. (1993) Cytotoxicity of antifolate inhibitors of thymidylate and purine synthesis to WiDr colonic carcinoma cells. *Cancer Res.*, 53, 5697-5706.
Yin, M.B., Guimaraes, M.A., Zhang, Z.G., Arredondo, M.A. and Rustum, Y.M. (1992) Time dependence of DNA lesions and growth inhibition by ICI D1694, a new quinazoline antifolate thymidylate synthase inhibitor. *Cancer Res.*, 52, 5900-5905.
Schmitz, J.C. and Chu, E. (2011) Effect of small interfering RNA 3'-end overhangs on chemosensitivity to thymidylate synthase inhibitors. *Silence*, 2, 1 (10 pages).

(Continued)

*Primary Examiner* — Richard Schnizer
(74) *Attorney, Agent, or Firm* — Dinesh Agarwal, P.C.

(57) ABSTRACT

A synthesized siRNA molecule having the sense strand with one or more uridine bases replaced by one or more respective nucleoside analogs, such as 5-fluoro-2'-deoxyuridine (FdU).

4 Claims, 6 Drawing Sheets

(56) References Cited

OTHER PUBLICATIONS

Houghton, P.J., Houghton, J.A., Germain, G. and Torrance, P.M. (1987) Development and characterization of a human colon adenocarcinoma xenograft deficient in thymidine salvage. *Cancer Res.*, 47, 2117-2122.

Laemmli, U.K. (1970) Cleavage of structural proteins during the assembly of the head of bacteriophage T4. *Nature*, 227, 680-685.

Matranga, C., Tomari, Y., Shin, C., Bartel, D.P. and Zamore, P.D. (2005) Passenger-strand cleavage facilitates assembly of siRNA into Ago2-containing RNAi enzyme complexes. *Cell*, 123, 607-620.

Chu, E., Koeller, D.M., Casey, J.L., Drake, J.C., Chabner, B.A., Elwood, P.C., Zinn, S. and Allegra, C.J. (1991) Autoregulation of human thymidylate synthase messenger RNA translation by thymidylate synthase. *Proc Natl Acad Sci*, 88, 8977-8981.

Khvorova, A., Reynolds, A. and Jayasena, S.D. (2003) Functional siRNAs and miRNAs exhibit strand bias. *Cell*, 115, 209-216.

Fridman, J.S. and Lowe, S.W. (2003) Control of apoptosis by p53. *Oncogene*, 22, 9030-9040.

Houghton, J.A., Harwood, F.G. and Tillman, D.M. (1997) Thymineless death in colon carcinoma cells is mediated via fas signaling. *Proc Natl Acad Sci*, 94, 8144-8149.

Reynolds, A., Leake, D., Boese, Q., Scaringe, S., Marshall, W.S. and Khvorova, A. (2004) Rational siRNA design for RNA interference. *Nature Biotechnology*, 22, 326-330.

Ui-Tei, K., Naito, Y., Zenno, S., Nishi, K., Yamato, K., Takahashi, F., Juni, A. and Saigo, K. (2008) Functional dissection of siRNA sequence by systematic DNA substitution: modified siRNA with a DNA seed arm is a powerful tool for mammalian gene silencing with significantly reduced off-target effect. *Nucleic Acids Res.*, 36, 2136-2151 (Pub. Online Feb. 11, 2008).

Duxbury, M.S., Ito, H., Zinner, M.J., Ashley, S.W. and Whang, E.E. (2004) RNA interference targeting the M2 subunit of ribonucleotide reductase enhances pancreatic adenocarcinoma chemosensitivity to gemcitabine. *Oncogene*, 23, 1539-1548.

Funamizu, N., Kamata, Y., Misawa, T., Uwagawa, T., Lacy, C.R., Yanaga, K. and Manome, Y. (2012) Hydroxyurea decreases gemcitabine resistance in pancreatic carcinoma cells with highly expressed ribonucleotide reductase. *Pancreas*, 41, 107-113.

Bijnsdorp, I.V., Schwendener, R.A., Schott, H., Fichtner, I., Smid, K., Laan, A.C., Schott, S., Losekoot, N., Honeywell, R.J. and Peters, G.J. (2011) Cellular pharmacology of multi- and duplex drugs consisting of ethynylcytidine and 5-fluoro-2'-deoxyuridine. *Investigational New Drugs*, 29, 248-257.

Gmeiner, W.H., Skradis, A., Pon, R.T. and Liu, J. (1999) Cytotoxicity and in-vivo tolerance of FdUMP[10]: a novel pro-drug of the TS inhibitory nucleotide FdUMP. *Nucleosides & Nucleotides*, 18, 1729-1730.

Ahn, J., Ko, A., Jun, E.J., Won, M., Kim, Y.K., Ju, E.S., Jeon, E.S. and Lee, H. (2012) Antiviral effects of siRNA simultaneously inducing RNA interference and type 1 interferon in coxsackievirus myocarditis. *Antimicrobial Agents and Chemotherapy*, 56, 3516-3523.

Bramsen, J.B. et al. (2009) A large-scale chemical modification screen identifies design rules to generate siRNAs with high activity, high stability and low toxicity. *Nucleic Acids Research*, vol. 37, No. 9, 2867-2881. Published Online Mar. 12, 2009.

Gmeiner, W.H. et al. (2010) Genome—Wide mRNA and microRNA Profiling of the NCI 60 Cell-Line Screen and Comparison of FdUMP[10] with Fluorouracil, Floxuridine, and Topoisomerase 1 Poisons, *Mol Cancer Ther*; 9(12); 3105-14.

\* cited by examiner

MODIFIED SIRNA MOLECULES INCORPORATING 5-FLUORO-2'-DEOXYURIDINE RESIDUES TO ENHANCE CYTOTOXICITY

CROSS-REFERENCE TO RELATED APPLICATIONS

The present application claims priority on prior U.S. Provisional Application Ser. No. 61/704,685, filed Sep. 24, 2012, which is hereby incorporated herein in its entirety by reference.

REFERENCE TO SEQUENCE LISTING

The present application contains a Sequence Listing (SEQ ID No: 1 to SEQ ID No: 23), which has been submitted in ASCII format via EFS-Web and is hereby incorporated by reference in its entirety. Said ASCII copy, created on Dec. 3, 2013, is named US1617-13_SL.txt and is 9,571 bytes in size.

STATEMENT REGARDING FEDERALLY SPONSORED RESEARCH OR DEVELOPMENT

The work leading to the present invention was supported by a Veterans Administration Merit Award (J.C.S.), National Natural Science Foundation of China (#30901823; S.W.), and by funds from the University of Pittsburgh Cancer Institute. The U.S. Government therefore has certain rights in the invention.

FIELD AND BACKGROUND OF THE INVENTION

The present invention is generally directed to cancer treatment and therapeutics, and more particularly to designing and synthesizing small interfering RNAs (siRNAs) having enhanced cytotoxicity.

Since their discovery over ten years ago, chemically-synthesized small interfering RNAs (siRNAs) have become the standard molecular biology tool for gene function studies. Their potential clinical application as therapeutic molecules is slowly becoming a reality due to improved delivery options. While significant challenges remain for the systemic delivery of siRNAs, several clinical trials have already documented the biological activity of siRNAs in target human tissues (References 1 and 2). The traditional approach has been to design a 19-mer double-stranded siRNA molecule consisting of two deoxythymidine (dT) nucleotide overhangs on either 3'-end (Reference 3). While dTdT overhangs have remained the standard overhang in siRNA synthesis, nearly any nucleotide can be used without incurring a deleterious effect on gene silencing (References 4 and 5). To enhance siRNA stability against nuclease degradation, nucleotides are often modified on the phosphate backbone and/or the ribose sugar moiety (Reference 6). These modifications are able to significantly extend the half-life of siRNAs in serum from minutes to days. In addition, these modifications are associated with a reduced number of off-target effects such as immune stimulation, passenger strand inactivation, and microRNA-like regulation (References 7 and 8). One issue that has yet to be addressed is the potential effect of these modified nucleotides on cellular metabolism following eventual intracellular degradation of the siRNA. Many anticancer and antiviral agents currently used in the clinical setting are nucleoside analogs (References 9 and 10). It is conceivable then that the modified nucleotides of siRNAs, once released from the siRNA molecule, might have potential impact on various cellular metabolic and signaling pathways.

Previous studies from our laboratory identified an siRNA molecule to potently and specifically inhibit thymidylate synthase (TS) expression (Reference 11). TS is a folate-dependent enzyme that catalyzes the reductive methylation of deoxyuridine monophosphate (dUMP) by the reduced folate 5,10-methylenetetrahydrofolate to thymidylate (dTMP) and dihydrofolate (Reference 12). dTMP is then metabolized to dTTP, an essential precursor for DNA biosynthesis. Although dTMP can be formed by phosphorylation of thymidine via the thymidine kinase-catalyzed pathway, the TS-mediated formation of dTMP provides for its sole intracellular de novo synthesis. Given its central role in DNA biosynthesis and given the observation that TS inhibition results in suppression of cellular proliferation, TS represents an important target for cancer chemotherapy (References 13 and 14).

One of the hallmarks of a TS inhibitor compound, such as raltitrexed, pemetrexed, and 5-fluoro-2'-deoxyuridine (FdU), is the ability of exogenous thymidine to rescue against its cytotoxic and antitumor effects (References 15 and 16). We have previously demonstrated that the growth inhibitory effects of a specific TS-targeted siRNA was completely reversed by thymidine suggesting that the siRNA specifically targets TS with minimal off-target effects on other genes that might impact cell growth and proliferation (Reference 11). Recent studies from our laboratory have shown that the intracellular degradation of siRNA released dT nucleosides from the 3'-end overhang, which, in turn, rescued against the cytotoxicity resulting from TS inhibition (Reference 17). This dT release was able to reverse the growth inhibitory effects of TS siRNA as well as the cytotoxic effects of small molecule inhibitors of TS, such as raltitrexed and FdU.

Given the observation that the released nucleosides from siRNAs have biological effects, we hypothesized that siRNA molecules could be rationally designed to contain specific nucleosides that, once degraded intracellularly, would release cytotoxic analogs and thereby enhance the therapeutic potential of the siRNA. Herein, we demonstrate that the fluoropyrimidine nucleoside 5-fluoro-2'-deoxyuridine (FdU) can be directly incorporated into the siRNA backbone, leading to enhanced cytotoxic and apoptotic effects.

ASPECTS OF THE INVENTION

The present disclosure is directed to various aspects of the present invention.

One aspect of the present invention is to provide a modified siRNA molecule having enhanced cytotoxic capability.

Another aspect of the present invention is to provide a modified siRNA molecule with a nucleoside analog that enhances its overall cytotoxic capability.

Another aspect of the present invention is to provide a modified siRNA molecule, which has inhibitory effects on the expression of TS protein.

Another aspect of the present invention is to provide a modified siRNA molecule, which has inhibitory effects on the expression of TS mRNA.

Another aspect of the present invention is to provide a modified siRNA molecule, which results in biological activity and/or cytotoxicity, particularly apoptotic effects on cancer cells, such as colon cancer cells.

Another aspect of the present invention is to provide a dual-acting siRNA molecule, which has gene-silencing effects, as well as enhanced cytotoxic and/or apoptotic effects.

Another aspect of the present invention is to provide a modified siRNA molecule, which can be used to develop therapeutic strategies to treat various diseases, particularly human cancers.

Another aspect of the present invention is to provide a modified siRNA sequence in which one or more uridine residues are replaced with a selected nucleoside analog(s). The nucleoside analog is preferably a cytotoxic agent.

Another aspect of the present invention is to provide a modified siRNA sequence in which one or more uridine residues are replaced with a pyrimidine nucleoside.

Another aspect of the present invention is to provide a modified siRNA sequence in which one or more uridine residues are replaced with a fluoropyrimidine nucleoside (FdU).

Another aspect of the present invention is to provide a nucleotide sequence as set forth in SEQ ID NO: 5, wherein the modified base represents 5-fluoro-2'-deoxyuridine (FdU).

Another aspect of the present invention is to provide a nucleotide sequence as set forth in SEQ ID NO: 7, wherein the modified base represents 5-fluoro-2'-deoxyuridine (FdU).

Another aspect of the present invention is to provide a nucleotide sequence as set forth in SEQ ID NO: 9, wherein the modified base represents 5-fluoro-2'-deoxyuridine (FdU).

Another aspect of the present invention is to provide a nucleotide sequence as set forth in SEQ ID NO: 13, wherein the modified base represents 5-fluoro-2'-deoxyuridine (FdU).

Another aspect of the present invention is to provide a nucleotide sequence as set forth in SEQ ID NO: 21, wherein the modified base represents 5-fluoro-2'-deoxyuridine (FdU).

Another aspect of the present invention is to provide a synthesized siRNA molecule having the sense strand with one or more uridine bases replaced by one or more respective nucleoside analogs.

BRIEF DESCRIPTION OF THE DRAWINGS

One of the above and other aspects, novel features and advantages of the present invention will become apparent from the following detailed description of the non-limiting preferred embodiment(s) of invention, illustrated in the accompanying drawings, wherein.

DETAILED DESCRIPTION OF THE PREFERRED EMBODIMENT(S) OF THE INVENTION

Figure 1:
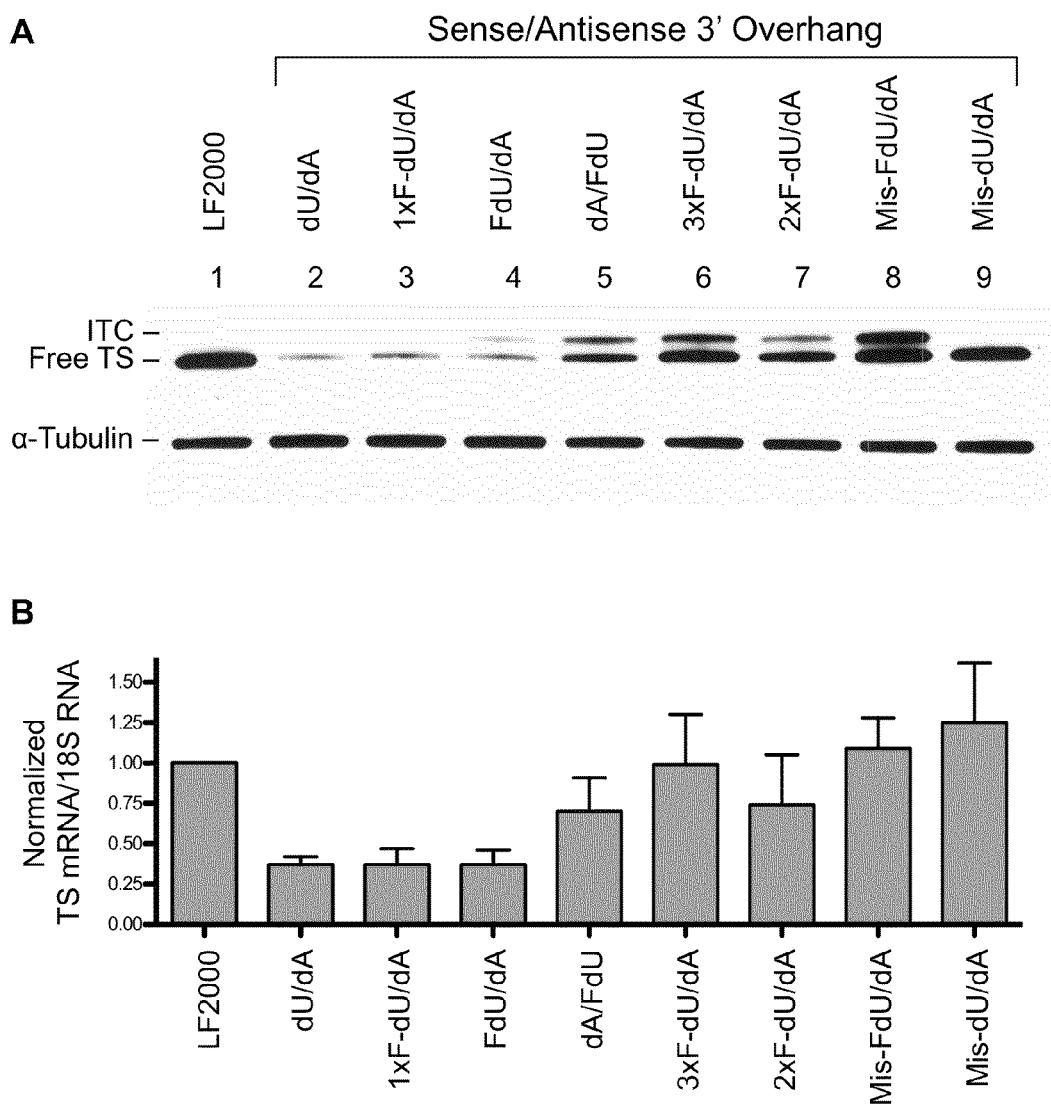
FIGS. 1A-B illustrate the effect of FdU incorporation in ssiRNA on TS protein expression. RKO cells were transfected with TS6 ssiRNAs (1 nM) containing various 3'-overhangs. After 6 hr, the medium was replaced. After an additional 48 hr, cells were harvested and processed for immunoblot and qPCR analysis as described in the Materials and Methods section. (A) Representative blot from 4 experiments. (B) All qPCR values represent the mean±S.D. from at least 3 separate experiments performed in triplicate. The normalized amount of TS mRNA from mock-transfected cells (LF2000) was set to 1.0 and all other values compared against that value. ITC, inhibitory ternary complex.

A few preferred embodiments of the present invention are described in detail sufficient for one skilled in the art to practice the present invention. It is understood, however, that the fact that a limited number of preferred embodiments are described herein does not in any way limit the scope of the present invention.

Therapeutic nucleic acids (antisense oligos and siRNAs) are usually composed of chemically-modified nucleotides. These modifications enhance RNA stability, confer improved pharmacokinetic properties, and increase target affinity. However, the precise fate of such modified nucleotides once the RNA is degraded within the cell is unknown. We previously demonstrated that a thymidylate synthase (TS)-targeted siRNA was rapidly degraded resulting in the intracellular release of individual nucleosides. The release of deoxythymidine from the 3'-overhang was sufficient to reverse the cytotoxic effects of the TS-targeted siRNA and other TS inhibitor compounds. We hypothesized that siRNA molecules could be designed with specific nucleoside analogs that, once released, would enhance the cytotoxicity of the siRNA. Extended 3'-overhang siRNAs termed 'sticky' siR- NAs (ssiRNAs) were designed that targeted TS mRNA and contained 5-fluoro-2'-deoxyuridine (FdU) moieties at various locations within the ssiRNA. After transfection into human colon RKO cancer cells, these ssiRNAs suppressed TS protein and TS mRNA expression with different efficiencies depending on the location of the FdU modification. FdU was rapidly released from the ssiRNA as evidenced by formation of the inhibitory ternary complex formed between TS protein and the FdU metabolite, FdUMP. Modification of the ssiRNA with FdU greatly enhanced cytotoxicity using both cell proliferation and clonogenic assays. The modified ssiRNA induced multiple DNA damage repair and apoptotic pathways when compared to the unmodified ssiRNA or the FdU-modified control ssiRNA. The strategy of designing siRNA molecules that incorporate cytotoxic nucleosides within their backbone represents a potentially novel drug development approach for the treatment of cancer and other human diseases.

Materials and Methods

RNA

RNAs and siRNAs were obtained from Dharmacon Research (ThermoScientific; Lafayette, Colo.), the University of Calgary Core DNA Services, and the W.M. Keck Oligonucleotide Synthesis Facility at Yale University. RNAs were resuspended in RNase-free water and allowed to anneal for 30 min at room temperature before aliquots were stored at −80° C. Synthesis of TS6 ssiRNA has been previously described (Reference 17). All TS6 siRNA/ssiRNA sequences are listed in Table 1 (below). A thymidine kinase-targeted siRNA was purchased from Dharmacon Research (Cat#D-006787-01).

Cell Culture

The human colon cancer RKO cell line, originally obtained from ATCC, has been previously well-characterized and was maintained in RPMI-1640 (Invitrogen; Carlsbad, Calif.) with 10% (v/v) dialyzed fetal bovine serum at 37° C. in a humidified incubator with 5% $CO_2$ (Reference 11). The thymidine kinase-deficient GC3/TK− cells were a gift from Dr. Janet Houghton (Reference 18). Cells were routinely authenticated by morphology and growth curve analysis. Cells were tested monthly for mycoplasma by the MycoAlert *Mycoplasma* detection assay (Cambrex BioScience; Rockland, Me.).

Transfection

Cells were plated at a density of $1.5 \times 10^5$ cells/well. On the following day, ssiRNAs were complexed with Lipofectamine 2000 (LF2000, Invitrogen) in serum-free RPMI-1640 medium and added to the plated cells. After 48 hr, cells were rinsed with PBS and scraped in cell lysis buffer (10 mM Tris pH7.4, 150 mM NaCl, 1 mM EDTA, 1% IGEPAL, 0.5% sodium deoxycholate, and 0.1% SDS) containing freshly added Protease Inhibitor Cocktail (Sigma; St. Louis, Mo.), 1 mM phenylmethylsulfonyl fluoride, and phosphatase inhibitors (Sigma). Lysates were sonicated and then centrifuged at 14,000 rpm for 30 min at 4° C. to remove debris. Cell lysates were stored at −80° C. for future use. For mRNA analysis, total RNA was extracted using Trizol (Invitrogen) and stored at −80° C. for future use.

Cell Proliferation Assay

RKO cells were plated in 96-well plates at a density of 800 cells/well. On the following day, cells were incubated with ssiRNA/LF2000 complexes for 6 hr, after which time, the growth medium was replaced, and cells were grown for an additional 96 hr. Similarly, RKO cells were treated with FdU (#F0503, Sigma) for 6 hr followed by medium replacement and then allowed to grow for an additional 96 hr. Cell proliferation/viability was quantified by the WST-1 assay (Roche; Indianapolis, Ind.).

Clonogenic Assay

RKO cells were plated in 6-well plates at a density of 600 cells/well. On the following day, cells were transfected with ssiRNA/LF2000 complexes for 6 hr after which time, the growth medium was replaced. Similarly, FdU was added to wells for 6 hr followed by medium replacement. After 8 days, cell colonies were fixed with Trypan blue solution (75% methanol/25% acetic acid/0.25% trypan blue), washed, and air-dried before counting colonies >50 cells.

Luciferase Assay

A DNA oligonucleotide corresponding to the TS6 siRNA target sequence (TS mRNA nt 1058-1077: 5'-GGAUAUU-GUCAGUCUUUAGG-3'- SEQ ID NO: 23) was annealed to its complimentary antisense sequence and ligated into the pGL3-Promoter plasmid (Promega; Madison, WI) at restriction sites Hind III and Nco I. The luciferase mRNA expressed from this plasmid was targeted by the antisense strand of TS6 siRNA. A second plasmid was constructed with the TS mRNA sequence inserted in the opposite orientation so that it could be targeted by the sense or passenger strand of TS6 siRNA. RKO cells were plated in 24-well plates at a density of $6 \times 10^4$ cells/well. On the following day, ssiRNAs (0.1 nM) and luciferase vectors (400 ng) were co-transfected into cells using LF2000. A renilla-expressing luciferase plasmid (pRL-SV40) (10 ng) was included in each transfection and used to normalize transfection conditions. After 24 hr, cells were washed with PBS, lysed in 1×PLG buffer, and firefly and renilla luciferase levels were determined by the Dual-Luciferase™ Reporter Assay system (Promega). Firefly luciferase activity values were divided by the renilla luciferase values to obtain a firefly/renilla ratio. Ratios obtained from transfection of the pGL3 plasmids in the absence of ssiRNA were set to 100%. Each experiment was performed in duplicate. Firefly/renilla ratios represent the mean ± S.D. from at least 4 separate experiments.

Immunoblot Analysis

Protein concentrations of cell lysates were determined using the DC Protein Assay (Bio-Rad; Hercules, Calif.). Equal amounts of protein (30 µg) from each cell lysate were resolved on SDS-PAGE using the method of Laemmli (Reference 19) and transferred onto 0.45 µm nitrocellulose membranes (Bio-Rad). Membranes were blocked and incubated overnight with primary antibodies at 4° C. The following antibodies were used in the experiments: anti-TS (Clone 4H4B1; Invitrogen), anti-TS (#5449; Cell Signaling; San Francisco, Calif.), anti-p21 Waf1/Cip1 (#2947; Cell Signaling), anti-p53 (#sc-126; Santa Cruz Biotechnology; Santa Cruz, Calif.), anti-PARP (#9542; Cell Signaling), anti-Fas (#4233; Cell Signaling), anti-phospho-histone H2A.X (Ser139) (#2577; Cell Signaling), anti-histone H2A.X (#7631; Cell Signaling), anti-phospho-ATM (pS1981; EPITOMICS Inc.; Burlingame, Calif.), anti-ATM (#A1106; Sigma), and anti-α-tubulin (EMD Biosciences; San Diego, Calif.). After multiple TBST washes (1×TBS, 0.1% Tween-20), membranes were incubated with corresponding horseradish peroxidase-conjugated secondary antibodies (Bio-Rad) for 1 hr at room temperature. Proteins were detected by the enhanced chemiluminescence method (SuperSignal West Pico substrate; Pierce; Rockford, Ill.). Quantitation of signal intensities was performed by densitometry on a Xerox scanner using NIH IMAGEJ software.

Odyssey System Immunoblot Analysis

Immunoblots were prepared as described above. After incubation with anti-TS polyclonal antibody, membranes were blocked with the Odyssey blocking buffer and incubated with IRDye 800CW goat anti-rabbit antibody (LI-COR Biosciences; Lincoln, Nebr., USA) according to the manufacturer instructions. The fluorescent signal was detected and quantified using the Odyssey infrared imaging system (LI-COR).

Real Time qRT-PCR Analysis

The first-strand cDNA was synthesized using 1.0 µg total RNA and the iScript™ Reverse Transcription Supermix for real-time quantitative polymerase chain reaction (qRT-PCR) (Bio-Rad; Hercules, Calif.). PCR was performed in triplicate using the SsoFast™ Probes Supermix (Bio-Rad) in a final reaction volume of 10 µL with gene-specific primer/probe sets, and a standard thermal cycling procedure (40 cycles) on a Bio-Rad CFX96™ Real-Time PCR System. mRNA levels of TS and 18S RNA were assessed using the TaqMan Gene Expression real-time PCR assays (Applied Biosystems; assay ID: Hs00426586_m1 and Hs03928990_g1, respectively). Results were expressed as the threshold cycle (Ct). The relative quantification of the target transcripts was determined by the comparative Ct method ($\Delta\Delta Ct$) according to the manufacturer's protocol. The $2^{-\Delta\Delta Ct}$ method was used to analyze the relative changes in gene expression. Control experiments without reverse transcription were performed to confirm that the total RNA was not contaminated with genomic DNA.

Flow Cytometry

RKO cells were plated in T-25 cm$^2$ flasks at a density of $2.5\times10^5$/flask. Cells were transfected on the following day with siRNA/LF2000 complexes for 6 hr. After medium replacement and additional incubation for 48 and 72 hr, respectively, cells were harvested, washed twice with PBS, resuspended in 1× binding buffer at a concentration of $1\times10^6$ cells/mL according to the manufacturer's protocol, stained with FITC Annexin V Apoptosis Detection Kit (BD Biosciences; San Jose, Calif.), and analyzed on the BD Accuri C6 Flow Cytometer (BD Accuri Cytometers Inc.; Ann Arbor, Mich.) at the UPCI Flow Cytometry Facility.

Statistical Analysis

All results are expressed as the mean±S.D. and represent data from at least 3 independent experiments. Student's t-tests (two tailed) were used to analyze differences between two groups, and P<0.05 was considered statistically significant.

Results

We had previously shown that the activity of 'sticky' siRNAs was at least equivalent or perhaps slightly more effective than standard siRNAs with respect to target mRNA suppression (Reference 17). However, in these studies, we determined that the extended dT overhangs on the ssiRNA were degraded, resulting in rescue from the cytotoxic effects of a TS-targeted ssiRNA. While this issue was eventually resolved by replacement of dT with dU, we hypothesized that this process of siRNA degradation might be used to release nucleoside moieties to further enhance the cytotoxicity associated with the siRNA. With this in mind, we designed and synthesized multiple TS-targeted ssiRNAs in which FdU analogs replaced uridine residues at various locations on the ssiRNA molecule (Table 1).

In our initial series of experiments, we determined whether the presence of FdU could alter the gene silencing effects of the TS-targeted ssiRNA. These modified ssiRNAs were transfected into human colon cancer RKO cells, and after a 48 hr incubation, Western blots and qPCR analyses were performed. As seen in FIG. 1A, the unmodified ssiRNA, TS6-dU/dA (5 dU on the 3'-end of the sense strand; 5 dA on the 3'-end of the antisense strand), at a concentration of 1 nM suppressed expression of TS protein by ~80% (FIG. 1A, lane 2) (quantified in Table 2). An ssiRNA (T56-1xF-dU/dA) with incorporation of a single FdU residue at the 4$^{th}$ position in the sense strand significantly inhibited expression of TS protein (FIG. 1A, lane 3). Of note, upon prolonged film exposure of the blot, a slower migrating band at approximately 38 kDa was also observed. This band presumably corresponds to the presence of the inhibitory ternary complex (ITC), which is made up of TS protein, the reduced folate 5,10-methylenetetrahydrofolate, and the fluoropyrimidine metabolite 5-fluoro-2'-deoxyuridine monophosphate (FdUMP) (Reference 12). The presence of this complex suggests that the ssiRNA was degraded resulting in the intracellular release of FdU, which would then be metabolized to the FdUMP metabolite. Similar effects were observed for an ssiRNA containing a single FdU residue at the 21$^{st}$ position on the sense strand (data not shown). Additional ssiRNA molecules were designed in which all of the 3'-end overhang dU nucleotides were replaced with FdU. Transfection of TS6-FdU/dA ssiRNA resulted in a similar inhibitory effect on TS protein expression (FIG. 1A, lane 4) when compared to the unmodified ssiRNA.

Figure 2:
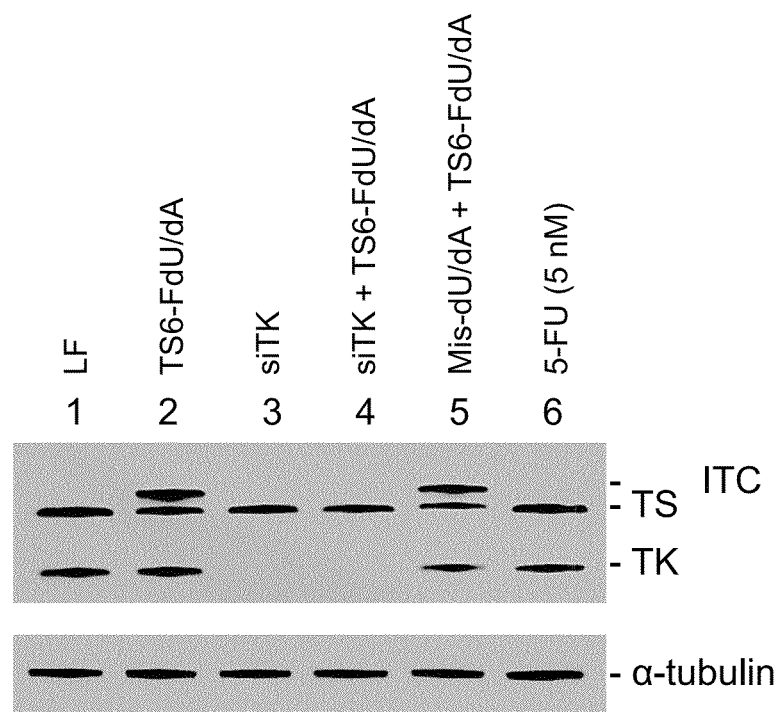
FIGS. 2A-B illustrate the effect of TK knockdown on the cytotoxicity of the FdU-modified ssiRNA. (A) RKO cells were transfected with 1 nM TK siRNA (lanes 3 and 4) or Mis-dU/dA (lane 5). After 6 hr, the medium was replaced with fresh medium. On the following day, cells were transfected with TS6-FdU/dA ssiRNA (1 nM) for 6 hr (lanes 2, 4, and 5) after which time, cells were harvested for immunoblot analysis. RKO cells were treated with 5-fluorouracil (5 nM) for 6 hr before harvesting (lane 6). (B) GC3/TK– cells were transfected with various concentrations of TS6-dU/dA or TS6-FdU/dA ssiRNA. After 6 hr, the medium was replaced and after an additional 5 days, cell proliferation was determined with the WST-1 assay.
Figure 2:
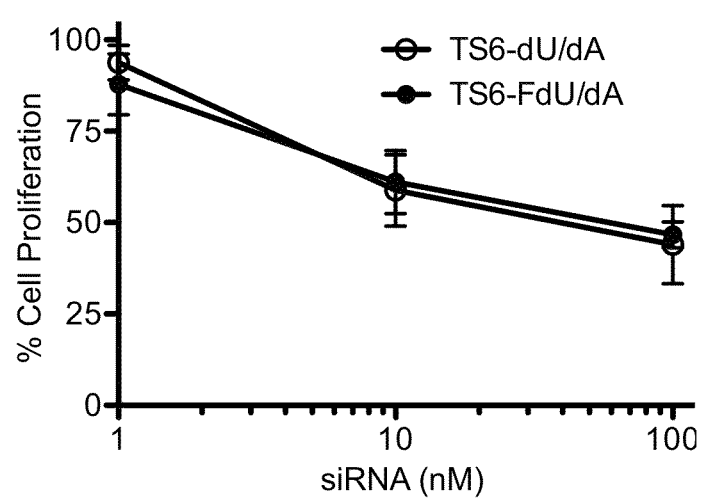

To gain further insight into the process of siRNA catabolism, experiments were performed to determine whether FdU analogs were released from degraded ssiRNAs as nucleosides or nucleotides. The FdU nucleoside is then phosphorylated by thymidine kinase to yield the 5-FU metabolite FdUMP. As seen in FIG. 2A, knockdown of thymidine kinase prevented formation of the ITC after transfection of TS6-FdU/dA (lane 4 vs. lane 2) suggesting that siRNAs are initially degraded into FdU nucleosides and that thymidine kinase is required for synthesis of FdUMP. While it is possible that FdU could be further catabolized to 5-fluorouracil (5-FU), incubation of RKO cells with 5-FU, at a concentration of 5 nM did not result in formation of the ITC (lane 6). This concentration was selected based on complete degradation of 1 nM TS6-FdU/dA and metabolism to 5-FU. Thus, analogs from these modified ssiRNAs are released in the form of nucleosides, which would then require further metabolism to yield active cytotoxic nucleotides.

It has been well-established that once siRNAs are incorporated into the RNA-induced silencing complex (RISC), the sense or non-targeting strand is degraded while the antisense strand remains bound in the RISC and guides mRNA cleavage (Reference 20). Since our previous work showed that pretreatment of TS siRNA, as opposed to simultaneous addition, enhanced cytotoxicity of TS inhibitors (Reference 11), we postulated that modification of the antisense strand with FdU residues might delay release of FdU allowing time for TS protein reduction by the siRNA. However, FdU modification of the 3'-end of antisense strand reduced the ability of the ssiRNA (TS6-dA/FdU) to suppress TS protein levels (FIG. 1, lane 5). We then designed ssiRNAs with internal modifications replacing U with FdU at positions 10, 16, and 18, respectively, in the antisense strand. This ssiRNA (TS6-3xF-dU/dA) was even less effective at targeting TS (FIG. 1, lane 6). Previous studies have shown that replacement of NTP for dNTP at the RISC cleavage site (position 10) has little impact on silencing (Reference 4). Thus, it appears that the fluorine atom on FdU somehow interfered with silencing. Transfection of the ssiRNA with FdU on positions 16 and 18 resulted in slight improvement in target knockdown (FIG. 1, lane 7); however, this modified ssiRNA was still less effective than the unmodified ssiRNA molecule (FIG. 1, lane 2). This finding suggests that placement of FdU within the antisense strand interferes with RNAi efficiency.

To separate the effects of siRNA knockdown function from that of nucleoside release, we synthesized a control, non-targeted ssiRNA containing 5 FdU residues on the sense strand (Mis-FdU/dA). This ssiRNA had absolutely no inhibitory effect on expression of TS protein (FIG. 1A, lane 8) or TS mRNA (FIG. 1B). Total levels of TS protein (free TS+ITC) were greater than what was observed in LF2000-treated cells, a finding that supports the negative autoregulatory model for TS translational regulation that our lab has previously identified (Reference 21). In this model, we proposed binding of TS inhibitor compounds to TS protein abrogates the normal interaction between TS protein and its own mRNA, thereby leading to increased mRNA translation and subsequent synthesis of new TS protein. Finally, the ability of each of these ssiRNAs to inhibit the expression of TS mRNA levels correlated with TS protein levels (FIG. 1B).

Figure 3:
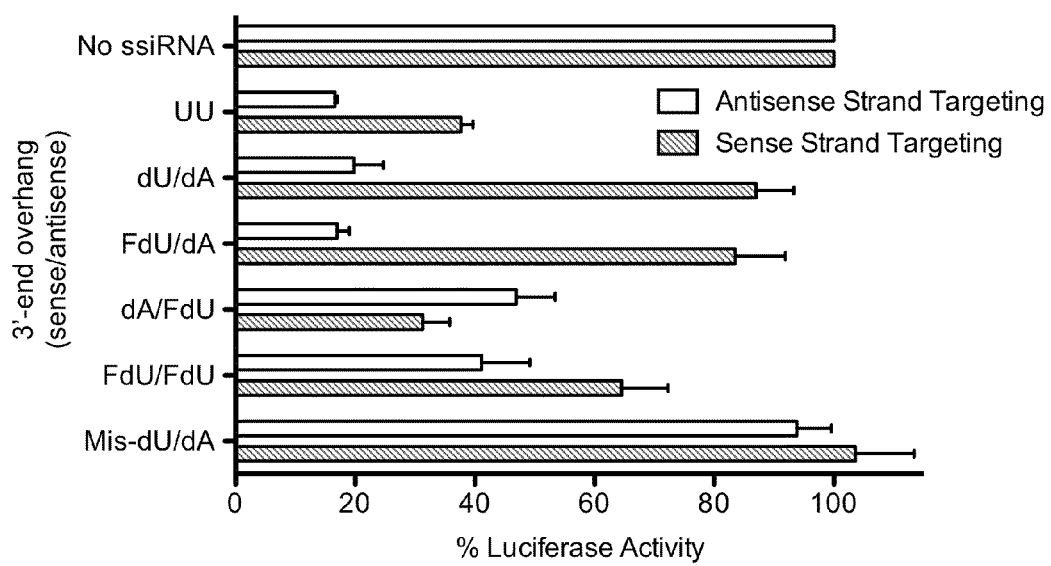
FIG. 3 illustrates the effect of 3'-end modification on ssiRNA strand selection. RKO cells were transfected with luciferase vectors (including the TS6 target site for either the antisense (open bars) or sense strand (hatched bars)) in combination with ssiRNAs containing different 3'-end overhangs. After 24 hr, cells were harvested and luciferase activity was determined as described in the Materials and Methods section. Firefly/renilla luciferase activity from vector-alone transfection was normalized to 100%. All values represent the mean±S.D. from at least 4 separate experiments performed in duplicate.

We next investigated whether FdU modifications might be altering the specific RNA strand that was actively incorporated into RISC. The respective 20-nt target site of the anti-sense and sense strands were cloned into separate luciferase-expressing plasmids. These plasmids were transfected into RKO cells with different ssiRNAs and luciferase activity was determined 24 hr later. As seen in FIG. 3, a standard TS6 siRNA with two uridine overhangs suppressed both anti-sense- and sense-strand guided targets. This inhibitory effect most likely resulted from the lack of a thermodynamic difference between the two ends of the TS6 siRNA resulting in an inability of RISC to select only one of the RNA strands (Reference 22). After transfection of TS6-dU/dA, antisense strand targeting was maintained while sense strand targeting was significantly reduced. This finding suggests that the 3'-end dU modification interferes with incorporation of the sense strand into RISC and provides an explanation for the slightly greater knockdown of TS previously observed with this ssiRNA (Reference 17). Transfection of the modified ssiRNA TS6-FdU/dA resulted in similar strand selection as with TS6-dU/dA. However, transfection of TS6-dA/FdU resulted in 2-fold less targeting by the antisense strand and enhanced sense strand targeting, suggesting that the FdU modification on the 3'-end is able to block RNA strand incorporation into RISC.

To further investigate the influence of 3'-end dU nucleotides on RNAi efficiency, additional ssiRNAs were designed and transfected into RKO cells. As seen in FIG. 4A, when the 3'-end overhang nucleotides were reversed from dU/dA to dA/dU, the ssiRNA was less able to suppress TS (FIG. 4A, lane 2 vs. lane 3). This effect was also seen at the mRNA level (FIG. 4B) and in the luciferase reporter assay (FIG. 4C) where the antisense targeting activity was reduced and the sense targeting activity was increased. Placing dU on both 3'-ends resulted in an ssiRNA (TS6-dU/dU) in which both strands had reduced targeting ability. Transfection of TS6-dA/dA ssiRNA resulted in efficient silencing by the antisense strand (knockdown of TS protein and mRNA) but suppressed the sense luciferase target (similar to UU overhang in FIG. 3). This result suggests that dA overhangs do not influence strand selection by RISC. Incorporation of ribonucleotides for the overhangs, as opposed to deoxynucleotides, the TS6-U/A ssiRNA effectively targeted TS protein and mRNA but demonstrated slightly more sense strand targeting than the deoxy version. These results suggest that either dU or FdU can block ssiRNA strand selection by RISC.

To determine whether FdU modifications enhance cytotoxicity of these ssiRNAs, cell proliferation and clonogenic assays were performed. As seen in Table 3, TS6-dU/dA had modest cytotoxic activity but displayed a greater effect on clonal growth with IC50 values of 81.92 and 1.77 nM respectively. Incorporation of one FdU residue into the ssiRNA (TS6-1xF-dU/dA) at the $4^{th}$ position enhanced the IC50 by nearly 30-fold for the cell growth assay and 5-fold for the clonogenic assay. Similar effects were observed for an ssiRNA containing a single FdU residue at the $21^{st}$ position on the sense strand (data not shown). Transfection of TS6-FdU/dA, which contains 5 FdU residues, resulted in further improvement in inhibition of cell growth and clonal growth with IC50 values of 0.81 and 0.17 nM, respectively. The ssiRNA TS6-dA/FdU was significantly less effective than the FdU-sense-modified ssiRNA in both assays (p=0.01 and p=0.005, respectively). This finding is in agreement with our Western blots and qPCR analyses, which show reduced effects on gene silencing by this particular ssiRNA. Modification of both 3'-ends with FdU (TS6-FdU/FdU) resulted in similar cytotoxic effects as TS6-FdU/dA. However, in the clonogenic assay, these additional FdU residues reduced efficacy by 2-fold as compared to TS6-FdU/dA (p=0.01). Thus, there may be a limit as to the total number of FdU residues that can enhance the overall cytotoxicity of the TS-targeted siRNA. Of note, the cytotoxic effects of these modified ssiRNAs were completely reversed by the addition of thymidine (10 uM; data not shown) suggesting that analog incorporation did not alter the TS6 ssiRNA specificity for its target mRNA.

As an important control, the unmodified TS6 mismatched ssiRNA had no effect on cell proliferation or clonogenic growth (data not shown). Transfection of a different control ssiRNA (Mis-FdU/dA) allowed us to begin to isolate the effect of TS knockdown from FdU release. The IC50 for this control ssiRNA was 2.88 nM in the WST-1 assay, which was similar to that observed with TS6-1xF-dU/dA, an active TS-targeted ssiRNA with a single FdU. Comparison between the non-targeted mismatch-FdU/dA and the targeted TS6-FdU/dA reveals that ssiRNA-mediated TS knockdown enhanced the IC50 by 3.5-fold in the growth assay. The effect is further enhanced in the clonogenic assay with a 10-fold lower IC50 value (0.17 versus 1.75 nM). To provide further evidence that the enhanced cytotoxicity was dependent upon FdU release with subsequent metabolism to FdUMP, RKO cells were transfected with a siRNA targeting thymidine kinase (TK) followed by subsequent transfection of TS6-FdU/dA. Unfortunately, these experiments were inconclusive as the TK siRNA was cytotoxic by itself. Thus, thymidine kinase-deficient GC3/TK– cells were utilized to compare the cytotoxicity of TS6-dU/dA and TS6-FdU/dA. Cell proliferation assays revealed that IC50 values of these two ssiRNAs were identical in these cells (51.4±27.8 nM and 45.9±18.6 nM, respectively) (FIG. 2B) confirming that FdU analogs are released from the ssiRNA as nucleosides and that TK is required for subsequent activation of FdU and enhancement of cytotoxicity.

Figure 5:
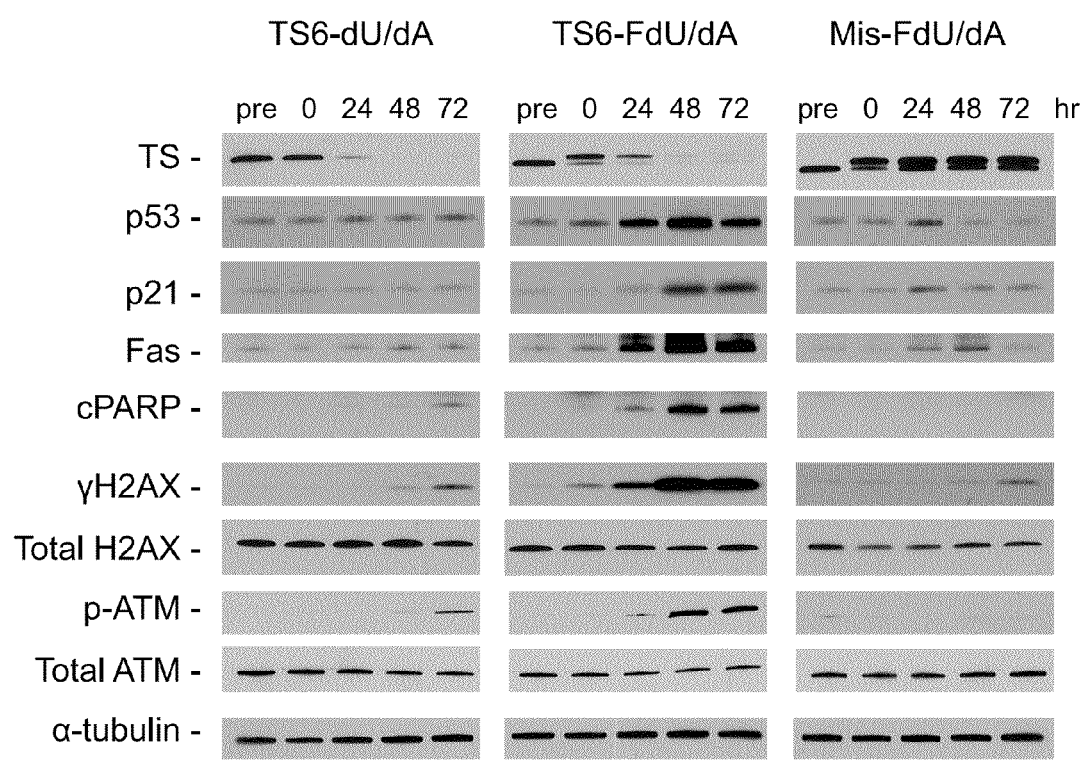
FIG. 5 illustrates time-dependent effects of FdU-containing ssiRNAs on protein expression. RKO cells were transfected with various TS6 ssiRNAs (10 nM). After 6 hr, the medium was replaced, and cells were harvested for immunoblot blot analysis at the following times: before39 transfection (pre) and 0, 24, 48, and 72 hr after transfection. Images shown are representative blots from at least 4 different experiments.

To investigate the associated cellular signaling pathways that are induced by these ssiRNAs, the expression of certain key proteins was analyzed. Immediately after transfection of TS6-FdU/dA or Mis-FdU/dA (0 hr), formation of the ITC is observed along with reduced levels of free TS suggesting that the ssiRNA was rapidly degraded releasing FdU (FIG. 5). The reduction in free TS at this early time point was not due to RNAi knockdown as TS protein levels were minimally affected after TS6-dU/dA transfection (left panel; pre vs. 0 hr). After 24 hr, TS protein levels were greatly decreased except after transfection of Mis-FdU/dA. It has been well-established that p53 is one of the first cellular proteins to respond to genotoxic stress (Reference 23). p53 levels are rapidly induced only after transfection of TS6-FdU/dA. The expression of the p53 responsive gene, p21, was subsequently induced. One of the hallmarks of 'thymineless death' due to TS inhibition is activation of the death receptor pathway (Reference 24). The receptor for this pathway, Fas, was upregulated after the FdU-modified TS-targeted ssiRNA but not by the other ssiRNAs. It has been reported that Fas activation triggers apoptosis (Reference 24). As seen in FIG. 5, cleaved PARP, a marker of apoptosis, was elevated only after TS6-FdU/dA transfection. Furthermore, two biomarkers of DNA damage, γH2AX and p-ATM, were strongly induced by TS6-FdU/dA with little to no effect in response to treatment with TS6-dU/dA or Mis-FdU/dA.

Figure 6:
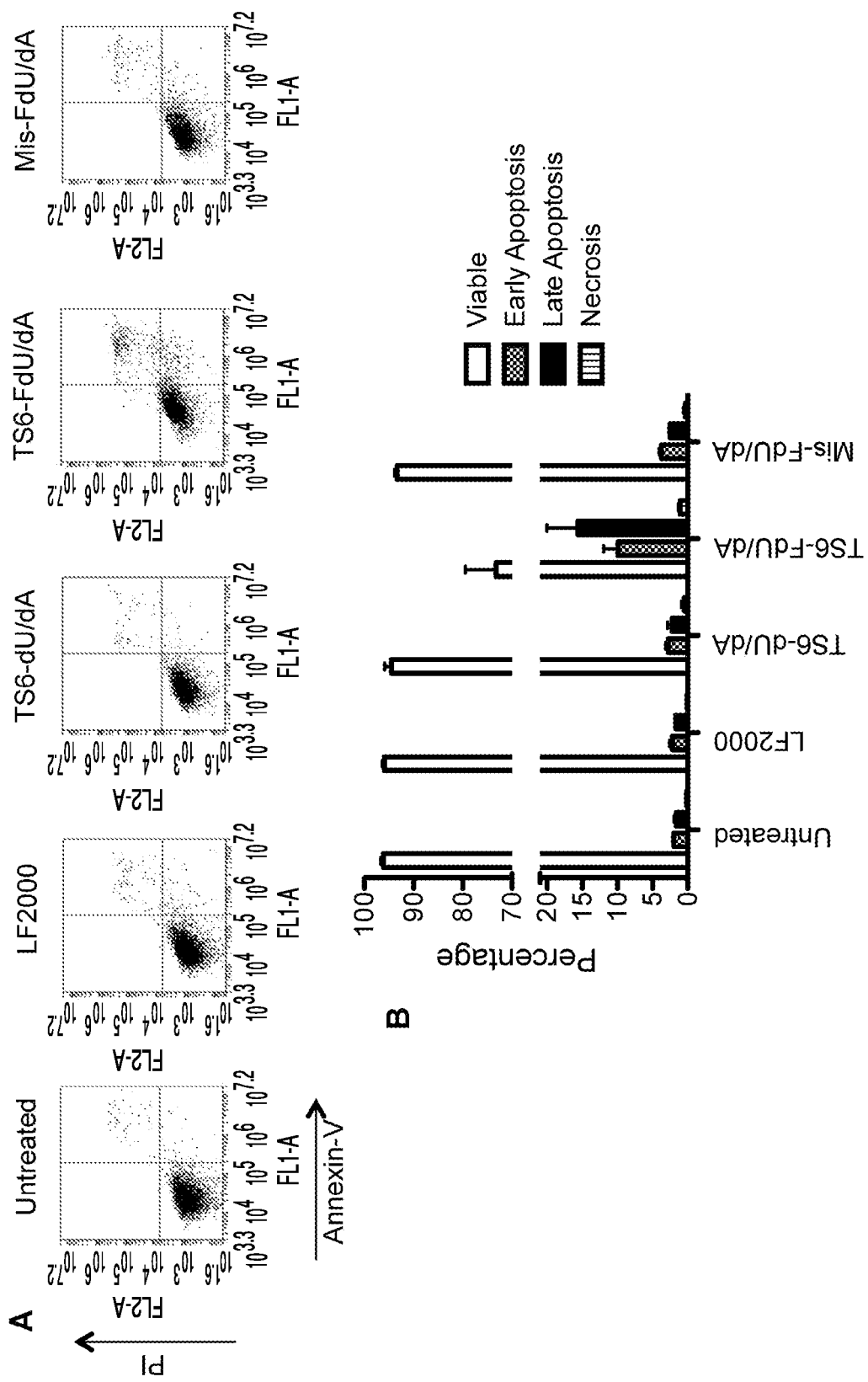
FIGS. 6A-B illustrate induction of apoptosis after transfection of FdU-containing ssiRNAs. RKO cells were transfected with various TS6 ssiRNAs (10 nM). After 6 hr, the medium was replaced with fresh medium. After 72 hr, cells were harvested, fixed, stained, and analyzed by flow cytometry as described in the Materials and Methods section. (A) Representative cytometry images from one experiment. Lower left quadrant represents viable cells; lower right quadrant, early apoptotic cells; upper right quadrant, late apoptotic cells; upper left quadrant, necrotic cells. (B) Percentage values represent the mean±S.D. from 3 separate experiments.

Finally, we performed a series of experiments to more directly investigate the effects of the modified ssiRNA on apoptosis. While smaller increases in apoptosis were observed after 48 hr (data not shown), transfection of TS6-FdU/dA resulted in a significant increase in both early and late apoptotic cells after 72 hr (FIG. 6). Transfection of the unmodified or mismatched ssiRNA had essentially no effect on inducing apoptosis. These results suggest that the combination of TS targeting with sRNA and TS enzyme inhibition from FdU released from degraded sRNA enhanced the ability of this modified sRNA to induce DNA damage and the process of apoptosis.

Discussion

The use of chemically-synthesized siRNAs has dramatically revolutionized the ability to investigate gene expression and function. Screens containing hundreds and even thousands of siRNAs can now be analyzed rapidly in various cancer cell models to identify critical genes and/or pathways required for a multitude of cellular responses. In contrast, the potential therapeutic application of sRNA has remained limited due to issues relating to sRNA stability, target selection, selective delivery, and cellular uptake. However, several of these issues, along with immune stimulation and miRNA-like effects, have been mostly resolved with advanced target selection algorithms and the use of chemically modified nucleotides (References 7 and 25). One issue that remains poorly defined is the effect of such modified nucleotides on cellular metabolism once the sRNA is eventually degraded within the cell. It is also unknown whether these nucleotides are eliminated from the cell or whether they might be directly incorporated into cellular RNA or DNA with resultant effects on synthesis and function.

In earlier studies, we had shown that traditional siRNAs and ssiRNAs with 3'-end dT overhangs are rapidly degraded after transfection with intracellular release of dT and other nucleosides (Reference 17). The release of these nucleosides was sufficient to rescue from the growth inhibitory effects of a TS-targeted siRNA. Moreover, transfection of a control, non-targeted siRNA with dT ends was able to rescue from the cytotoxic effects of TS inhibitor compounds. Taken together, these findings suggested that the actual composition of the siRNA molecule itself might be critically important in determining its eventual cytotoxic effects and that its subsequent degradation would lead to the release of individual nucleosides and thereby impact on cellular nucleotide pools.

Figure 4:
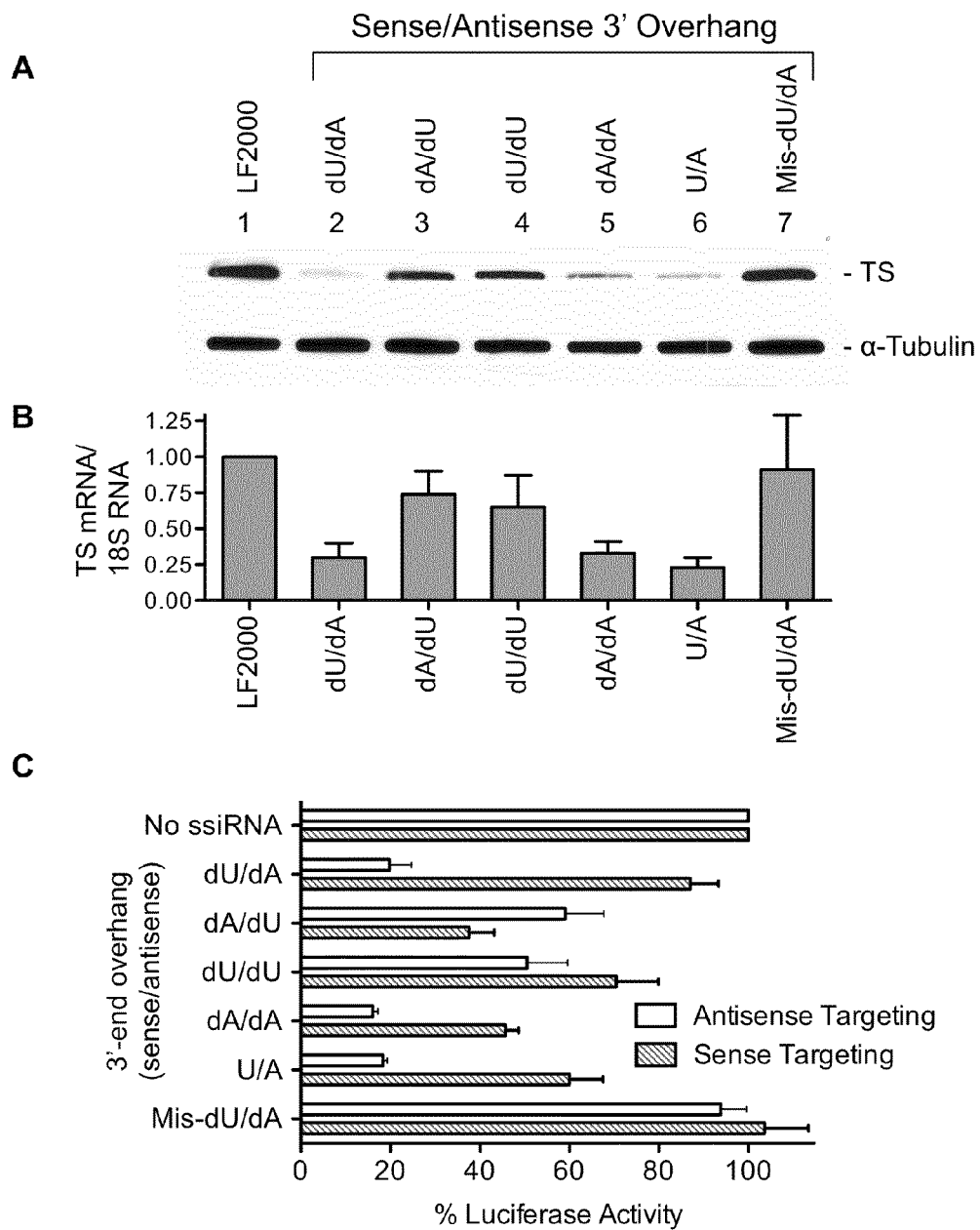
FIGS. 4A-C illustrate the effect of 3'-end dU incorporation on ssiRNA strand selection. RKO cells were transfected with various TS6 ssiRNAs (1 nM) for 6 hr. After an additional 48 hr, cells were harvested for immunoblot (A) and qPCR (B) analysis. (C) Luciferase vectors (containing the siRNA target site for either the sense or antisense strand) were transfected into RKO cells in combination with different ssiRNAs. After 24 hr, cells were harvested and luciferase activity was determined as described in the Materials and Methods section. Luciferase activity from vector-alone transfection was normalized to 100%. All values represent the mean±S.D. from at least 4 separate experiments performed in duplicate.

To exploit this process of siRNA degradation, we hypothesized that a siRNA molecule could be designed with nucleoside analogs that would enhance its overall cytotoxic effects. In this regard, we have shown that FdU can be incorporated into a TS-targeted ssiRNA with improved cytotoxicity. As the modified ssiRNA was degraded, FdU was released which, after further metabolism by thymidine kinase to FdUMP, formed an inhibitory ternary complex (ITC) with TS protein (appears as the slower migrating TS band in FIG. 1A). As with all chemically modified nucleotides, their specific location on the siRNA plays a critical role in determining the eventual gene silencing activity (References 4 and 7). Our studies have shown that internal modifications within the antisense strand were not well tolerated as the gene silencing effects on TS expression were completely abrogated. Incorporation of FdU into the 3'-overhang of the ssiRNA blocked the modified RNA strand from being incorporated into the RISC complex (FIG. 3). Interestingly, this effect was also observed with 3'-end dU nucleotides but not dA (FIG. 4). At this point, it is unclear as to why dU or FdU would block RNAi strand selection as previous studies have shown that siRNAs appear to be quite tolerant of deoxynucleotide substitutions on the 3'-end (Reference 26).

The incorporation of FdU moieties into the ssiRNA greatly enhanced its cytotoxic effects. The addition of one FdU into the ssiRNA backbone reduced the IC50 value by 27-fold using WST-1 assay and by 5-fold using the clonogenicity assay (Table 3). Incorporation of 5 FdU on the 3'-end of the sense strand further enhanced siRNA toxicity (T56-FdU/dA). Modification of both strands with FdU did not provide any additional enhancement of either cytotoxicity or clonogenicity. In the clonal assay, the unmodified TS-targeted ssiRNA and the untargeted control, FdU-modified ssiRNA yielded similar IC50 values suggesting that both approaches (siRNA knockdown and nucleoside analog release) were effective at growth inhibition. However, combining both approaches into a single ssiRNA enhanced growth inhibitory effects by 10-fold providing further support for our initial hypothesis. Previously, we demonstrated that resistant colon cancer cells could be re-sensitized to TS inhibitor compounds using our TS-targeted siRNA (Reference 11). Taken together, these results support the potential advantage of such a combined approach.

The design and synthesis of modified siRNAs with nucleoside analogs appears promising. The rationale for considering the incorporation of various nucleoside analogs comes from the fact that they have been used widely for antiviral and anticancer treatment (References 9 and 10). In particular, it is conceivable that ssiRNAs or siRNAs that incorporate HIV nucleoside analogs, such as stavudine and emtricitabine, or anticancer agents such as gemcitabine, cytarabine, fludarabine, and decitabine, could be easily synthesized. The incorporation of such modifications in ssi/siRNAs might then give rise to molecules with enhanced cytotoxicity. For instance, a synergistic effect might be observed with a gemcitabine-containing siRNA that suppresses the key DNA synthesis enzyme, ribonucleotide reductase (RRM1). Two groups have demonstrated that siRNAs directed against RRM1 can enhance gemcitabine toxicity in multiple cancer cell lines (References 27 and 28). Currently, modified nucleotides are incorporated into siRNAs or antisense oligonucleotides to enhance RNA stability against nucleases and to increase their binding affinity for their target mRNA (Reference 4). There have been several reports in which two or more nucleoside analogs are joined together to form 'prodrug'-like molecules that depend upon intracellular degradation for cytotoxicity (References 29 and 30). More recently, it was shown that the incorporation of a 5'-triphosphate on a viral-specific siRNA was able to enhance potency due to an innate immune response activated by the 5'-triphosphate (Reference 31).

In conclusion, we have designed a novel dual-acting siRNA molecule, which to our knowledge, is the first of its class to have been developed. This siRNA has the usual gene silencing effects typically seen with siRNAs. However, within the backbone of the siRNA, we have incorporated the fluoropyrimidine nucleoside FdU, which when released upon siRNA degradation, can be metabolized via successive phosphorylation steps to nucleotide metabolites that then have biological activity and cytotoxicity. Of importance, this dual-acting siRNA displays enhanced cytotoxic and apoptotic effects when compared to the more traditionally designed TS-targeted siRNA. With the rapid development of nanoparticle delivery technologies, such modified siRNAs may find clinical value to be used as monotherapy or in combination with other chemotherapy agents to treat a wide range of human cancers. Moreover, this strategy of dual-acting siRNAs represents a potentially novel drug development approach for the treatment of other human diseases.

TABLE 1 ssiRNA Sequences

| ssiRNA | Nucleotide Sequence |
|---|---|
| TS6-UU | 5'-GGAUAUUGUCAGUCUUUAGG-UU-'3 (SEQ ID NO: 1)<br>3'-UU-CCUAUAACAGUCAGAAAUCC-'5 (SEQ ID NO: 2) |
| TS6-dU/dA | 5'-GGAUAUUGUCAGUCUUUAGG-dUdUdUdUdU-'3 (SEQ ID NO: 3)<br>3'-dAdAdAdAdA-CCUAUAACAGUCAGAAAUCC-'5 (SEQ ID NO: 4) |
| TS6-1xF-dU/dA<br>($4^{th}$ position) | 5'-GGAFAUUGUCAGUCUUUAGG-dUdUdUdUdU-'3 (SEQ ID NO: 5)<br>3'-dAdAdAdAdA-CCUAUAACAGUCAGAAAUCC-'5 (SEQ ID NO: 6) |
| TS6-1xF-dU/dA<br>($21^{st}$ position) | 5'-GGAUAUUGUCAGUCUUUAGG-FdUdUdUdU-'3 (SEQ ID NO: 7)<br>3'-dAdAdAdAdA-CCUAUAACAGUCAGAAAUCC-'5 (SEQ ID NO: 8) |
| TS6-FdU/dA | 5'-GGAUAUUGUCAGUCUUUAGG-FFFFF-'3 (SEQ ID NO: 9)<br>3'-dAdAdAdAdA-CCUAUAACAGUCAGAAAUCC-'5 (SEQ ID NO: 10) |
| TS6-dA/FdU | 5'-GGAUAUUGUCAGUCUUUAGG-dAdAdAdAdA-'3 (SEQ ID NO: 11)<br>3'-FFFFF-CCUAUAACAGUCAGAAAUCC-'5 (SEQ ID NO: 12) |
| TS6-FdU/FdU | 5'-GGAUAUUGUCAGUCUUUAGG-FFFFF-'3 (SEQ ID NO: 13)<br>3'-FFFFF-CCUAUAACAGUCAGAAAUCC-'5 (SEQ ID NO: 14) |
| TS6-3xF-dU/dA | 5'-GGAUAUUGUCAGUCUUUAGG-dUdUdUdUdU-'3 (SEQ ID NO: 15)<br>3'-dAdAdAdAdA-CCFAFAACAGFCAGAAAUCC-'5 (SEQ ID NO: 16) |
| TS6-2xF-dU/dA | 5'-GGAUAUUGUCAGUCUUUAGG-dUdUdUdUdU-'3 (SEQ ID NO: 17)<br>3'-dAdAdAdAdA-CCFAFAACAGUCAGAAAUCC-'S (SEQ ID NO: 18) |
| Mis-dU/dA | 5'-GGAUACUGCCAAUCUCUAGG-dUdUdUdUdU-'3 (SEQ ID NO: 19)<br>3'-dAdAdAdAdA-CCUAUGACGGUUAGAGAUCC-'5 (SEQ ID NO: 20) |
| Mis-FdU/dA | 5'-GGAUACUGCCAAUCUCUAGG-FFFFF-'3 (SEQ ID NO: 21)<br>3'-dAdAdAdAdA-CCUAUGACGGUUAGAGAUCC-'5 (SEQ ID NO: 22) |

The top strand is the sense (passenger) strand with the bottom strand being the antisense (guide) strand of the ssiRNA.
Bolded and underlined nucleotides (F) are 5-fluoro-2'-deoxyuridine (FdU).
Nucleotides that are only bolded are mismatched nucleotides.

TABLE 2

Quantitation of free versus ITC-bound TS protein

| ssiRNA | Free TS (%) | ITC-Bound TS (%) |
|---|---|---|
| LF2000 | 100 | — |
| TS6-dU/dA | 22.6 ± 7.5 | — |
| TS6-1xF-dU/dA | 27.3 ± 8.3 | 4.4 ± 2.6 |
| TS6-FdU/dA | 29.8 ± 12.0 | 22.0 ± 11.8 |
| TS6-dA/FdU | 48.0 ± 18.6 | 30.6 ± 15.6 |
| TS6-3xF-dU/dA | 73.6 ± 14.7 | 26.2 ± 10.7 |
| TS6-2xF-dU/dA | 54.1 ± 14.1 | 15.4 ± 9.5 |
| Mis-FdU/dA | 89.5 ± 26.2 | 45.6 ± 21.1 |
| Mis-dU/dA | 90.1 ± 14.0 | — |

TS protein levels in immunoblots were quantified using an Odyssey LICOR scanner. Values represent the mean ± S.D. from 6 separate experiments. All values are normalized to the amount of free TS protein in mock-transfected cells (LF2000) set to 100%.

TABLE 3

Effect of ssiRNA sequence on cell growth and clonal growth.

| | IC50 (nM) | |
|---|---|---|
| ssiRNA | WST-1 | Clonogenic |
| TS6-dU/dA | 81.92 ± 37.15 | 1.77 ± 1.02 |
| TS6-1xF-dU/dA | 2.85 ± 0.83 | 0.34 ± 0.08 |
| TS6-FdU/dA | 0.81 ± 0.29 | 0.17 ± 0.06 |

TABLE 3-continued

Effect of ssiRNA sequence on cell growth and clonal growth.

| | IC50 (nM) | |
|---|---|---|
| ssiRNA | WST-1 | Clonogenic |
| TS6-dA/FdU | 1.27 ± 0.32 | 0.40 ± 0.20 |
| TS6-FdU/FdU | 0.77 ± 0.12 | 0.43 ± 0.16 |
| Mis-FdU/dA | 2.88 ± 0.88 | 1.75 ± 0.46 |
| FdU (TS inhibitor) | 6.93 ± 2.08 | 7.42 ± 1.33 |

IC50 values denote the concentration that inhibits 50% of cell or clonal growth. Values represent the mean ± S.D. from at least 3 separate experiments.

While this invention has been described as having preferred sequences, ranges, steps, order of steps, materials, structures, symbols, indicia, graphics, color scheme(s), shapes, configurations, features, components, or designs, it is understood that it is capable of further modifications, uses and/or adaptations of the invention following in general the principle of the invention, and including such departures from the present disclosure as those come within the known or customary practice in the art to which the invention pertains, and as may be applied to the central features hereinbefore set forth, and fall within the scope of the invention and of the limits of the claims appended hereto or presented later. The invention, therefore, is not limited to the preferred embodiment(s) shown/described herein.

REFERENCES

The following references, and those cited in the disclosure herein, are hereby incorporated herein in their entirety by reference.

1. Burnett, J. C. and Rossi, J. J. (2012) RNA-based therapeutics: current progress and future prospects. *Chemistry & Biology*, 19, 60-71.
2. DeVincenzo, J., Lambkin-Williams, R., Wilkinson, T., Cehelsky, J., Nochur, S., Walsh, E., Meyers, R., Gollob, J. and Vaishnaw, A. (2010) A randomized, double-blind, placebo-controlled study of an RNAi-based therapy directed against respiratory syncytial virus. *Proc Natl Acad Sci*, 107, 8800-8805.
3. Elbashir, S. M., Harborth, J., Lendeckel, W., Yalcin, A., Weber, K. and Tuschl, T. (2001) Duplexes of 21-nucleotide RNAs mediate RNA interference in cultured mammalian cells. *Nature*, 411, 494-498.
4. Chiu, Y. L. and Rana, T. M. (2003) siRNA function in RNAi: a chemical modification analysis. *RNA*, 9, 1034-1048.
5. Elbashir, S. M., Martinez, J., Patkaniowska, A., Lendeckel, W. and Tuschl, T. (2001) Functional anatomy of siRNAs for mediating efficient RNAi in *Drosophila melanogaster* embryo lysate. *The EMBO J*, 20, 6877-6888.
6. Watts, J. K., Deleavey, G. F. and Damha, M. J. (2008) Chemically modified siRNA: tools and applications. *Drug Discovery Today*, 13, 842-855.
7. Jackson, A. L., Burchard, J., Leake, D., Reynolds, A., Schelter, J., Guo, J., Johnson, J. M., Lim, L., Karpilow, J., Nichols, K. et al. (2006) Position-specific chemical modification of siRNAs reduces "off-target" transcript silencing. *RNA*, 12, 1197-1205.
8. Judge, A. D., Bola, G., Lee, A. C. and MacLachlan, I. (2006) Design of noninflammatory synthetic siRNA mediating potent gene silencing in vivo. *Molecular Therapy: J of the American Society of Gene Therapy*, 13, 494-505.
9. Cihlar, T. and Ray, A. S. (2010) Nucleoside and nucleotide HIV reverse transcriptase inhibitors: 25 years after zidovudine. *Antiviral Res.*, 85, 39-58.
10. Sampath, D., Rao, V. A. and Plunkett, W. (2003) Mechanisms of apoptosis induction by nucleoside analogs. *Oncogene*, 22, 9063-9074.
11. Schmitz, J. C., Chen, T. M. and Chu, E. (2004) Small interfering double-stranded RNAs as therapeutic molecules to restore chemosensitivity to thymidylate synthase inhibitor compounds. *Cancer Res*, 64, 1431-1435.
12. Carreras, C. W. and Santi, D. V. (1995) The catalytic mechanism and structure of thymidylate synthase. *Annual Review of biochemistry*, 64, 721-762.
13. Danenberg, P. V. (1977) Thymidylate synthetase—a target enzyme in cancer chemotherapy. *Biochimica et Biophysica Acta*, 473, 73-92.
14. Shoichet, B. K., Stroud, R. M., Santi, D. V., Kuntz, I. D. and Perry, K. M. (1993) Structure-based discovery of inhibitors of thymidylate synthase. *Science*, 259, 1445-1450.
15. Smith, S. G., Lehman, N. L. and Moran, R. G. (1993) Cytotoxicity of antifolate inhibitors of thymidylate and purine synthesis to WiDr colonic carcinoma cells. *Cancer Res.*, 53, 5697-5706.
16. Yin, M. B., Guimaraes, M. A., Zhang, Z. G., Arredondo, M. A. and Rustum, Y. M. (1992) Time dependence of DNA lesions and growth inhibition by ICI D1694, a new quinazoline antifolate thymidylate synthase inhibitor. *Cancer Res.*, 52, 5900-5905.
17. Schmitz, J. C. and Chu, E. (2011) Effect of small interfering RNA 3'-end overhangs on chemosensitivity to thymidylate synthase inhibitors. *Silence*, 2, 1.
18. Houghton, P. J., Houghton, J. A., Germain, G. and Torrance, P. M. (1987) Development and characterization of a human colon adenocarcinoma xenograft deficient in thymidine salvage. *Cancer Res.*, 47, 2117-2122.
19. Laemmli, U. K. (1970) Cleavage of structural proteins during the assembly of the head of bacteriophage T4. *Nature*, 227, 680-685.
20. Matranga, C., Tomari, Y., Shin, C., Bartel, D. P. and Zamore, P. D. (2005) Passenger-strand cleavage facilitates assembly of siRNA into Ago2-containing RNAi enzyme complexes. *Cell*, 123, 607-620.
21. Chu, E., Koeller, D. M., Casey, J. L., Drake, J. C., Chabner, B. A., Elwood, P. C., Zinn, S. and Allegra, C. J. (1991) Autoregulation of human thymidylate synthase messenger RNA translation by thymidylate synthase. *Proc Natl Acad Sci*, 88, 8977-8981.
22. Khvorova, A., Reynolds, A. and Jayasena, S. D. (2003) Functional siRNAs and miRNAs exhibit strand bias. *Cell*, 115, 209-216.
23. Fridman, J. S. and Lowe, S. W. (2003) Control of apoptosis by p53. *Oncogene*, 22, 9030-9040.
24. Houghton, J. A., Harwood, F. G. and Tillman, D. M. (1997) Thymineless death in colon carcinoma cells is mediated via fas signaling. *Proc Natl Acad Sci*, 94, 8144-8149.
25. Reynolds, A., Leake, D., Boese, Q., Scaringe, S., Marshall, W. S. and Khvorova, A. (2004) Rational siRNA design for RNA interference. *Nature Biotechnology*, 22, 326-330.
26. Ui-Tei, K., Naito, Y., Zenno, S., Nishi, K., Yamato, K., Takahashi, F., Juni, A. and Saigo, K. (2008) Functional dissection of siRNA sequence by systematic DNA substitution: modified siRNA with a DNA seed arm is a powerful tool for mammalian gene silencing with significantly reduced off-target effect. *Nucleic Acids Res.*, 36, 2136-2151.
27. Duxbury, M. S., Ito, H., Zinner, M. J., Ashley, S. W. and Whang, E. E. (2004) RNA interference targeting the M2 subunit of ribonucleotide reductase enhances pancreatic adenocarcinoma chemosensitivity to gemcitabine. *Oncogene*, 23, 1539-1548.
28. Funamizu, N., Kamata, Y., Misawa, T., Uwagawa, T., Lacy, C. R., Yanaga, K. and Manome, Y. (2012) Hydroxyurea decreases gemcitabine resistance in pancreatic carcinoma cells with highly expressed ribonucleotide reductase. *Pancreas*, 41, 107-113.
29. Bijnsdorp, I. V., Schwendener, R. A., Schott, H., Fichtner, I., Smid, K., Laan, A. C., Schott, S., Losekoot, N., Honeywell, R. J. and Peters, G. J. (2011) Cellular pharmacology of multi- and duplex drugs consisting of ethynylcytidine and 5-fluoro-2'-deoxyuridine. *Investigational New Drugs*, 29, 248-257.
30. Gmeiner, W. H., Skradis, A., Pon, R. T. and Liu, J. (1999) Cytotoxicity and in-vivo tolerance of FdUMP[10]: a novel pro-drug of the TS inhibitory nucleotide FdUMP. *Nucleosides & Nucleotides*, 18, 1729-1730.
31. Ahn, J., Ko, A., Jun, E. J., Won, M., Kim, Y. K., Ju, E. S., Jeon, E. S. and Lee, H. (2012) Antiviral effects of siRNA simultaneously inducing RNA interference and type 1 interferon in coxsackievirus myocarditis. *Antimicrobial Agents and Chemotherapy*, 56, 3516-3523.

What is claimed is:

1. A nucleic acid comprising the nucleotide sequence of SEQ ID NO: 5, wherein position 4 of SEQ ID NO: 5 is a 5-fluoro-2'-deoxyuridine (FdU) residue.

2. A nucleic acid comprising the nucleotide sequence of SEQ ID NO: 7, wherein position 21 of SEQ ID NO: 7 is a 5-fluoro-2'-deoxyuridine (FdU) residue.

3. A nucleic acid comprising the nucleotide sequence of SEQ ID NO: 9, wherein positions 21-25 of SEQ ID NO: 9 are 5-fluoro-2'-deoxyuridine (FdU) residues.

4. A nucleic acid comprising the nucleotide sequence of SEQ ID NO: 21, wherein positions 21-25 of SEQ ID NO: 21 are 5-fluoro-2'-deoxyuridine (FdU) residues.

* * * * *

SEQUENCE LISTING

<160> NUMBER OF SEQ ID NOS: 23

<210> SEQ ID NO 1
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
ggauauuguc agucuuuagg uu                                              22

<210> SEQ ID NO 2
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
ccuaaagacu gacaauaucc uu                                              22

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (21)..(25)
<223> OTHER INFORMATION: deoxyuridine

<400> SEQUENCE: 3
ggauauuguc agucuuuagg uuuuu                                           25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (21)..(25)
<223> OTHER INFORMATION: deoxyadenosine

<400> SEQUENCE: 4
ccuaaagacu gacaauaucc aaaaa                                           25

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide -continued

```
<220> FEATURE:
<221> NAME/KEY: modified_base
<222> LOCATION: (4)..(4)
<223> OTHER INFORMATION: 5-fluoro-2'-deoxyuridine
<220> FEATURE:
<221> NAME/KEY: modified_base
<222> LOCATION: (21)..(25)
<223> OTHER INFORMATION: deoxyuridine

<400> SEQUENCE: 5
ggauauuguc agucuuuagg uuuuu                                          25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (21)..(25)
<223> OTHER INFORMATION: deoxyadenosine

<400> SEQUENCE: 6
ccuaaagacu gacaauaucc aaaaa                                          25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (21)..(21)
<223> OTHER INFORMATION: 5-fluoro-2'-deoxyuridine
<220> FEATURE:
<221> NAME/KEY: modified_base
<222> LOCATION: (22)..(25)
<223> OTHER INFORMATION: deoxyuridine

<400> SEQUENCE: 7
ggauauuguc agucuuuagg uuuuu                                          25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (21)..(25)
<223> OTHER INFORMATION: deoxyadenosine

<400> SEQUENCE: 8
ccuaaagacu gacaauaucc aaaaa                                          25

<210> SEQ ID NO 9
```

```
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (21)..(25)
<223> OTHER INFORMATION: 5-fluoro-2'-deoxyuridine

<400> SEQUENCE: 9
ggauauuguc agucuuuagg uuuuu                                         25

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (21)..(25)
<223> OTHER INFORMATION: deoxyadenosine

<400> SEQUENCE: 10
ccuaaagacu gacaauaucc aaaaa                                         25

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (21)..(25)
<223> OTHER INFORMATION: deoxyadenosine

<400> SEQUENCE: 11
ggauauuguc agucuuuagg aaaaa                                         25

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (21)..(25)
<223> OTHER INFORMATION: 5-fluoro-2'-deoxyuridine

<400> SEQUENCE: 12
ccuaaagacu gacaauaucc uuuuu                                         25
```

```
<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (21)..(25)
<223> OTHER INFORMATION: 5-fluoro-2'-deoxyuridine

<400> SEQUENCE: 13
ggauauuguc agucuuuagg uuuuu                                              25

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (21)..(25)
<223> OTHER INFORMATION: 5-fluoro-2'-deoxyuridine

<400> SEQUENCE: 14
ccuaaagacu gacaauaucc uuuuu                                              25

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (21)..(25)
<223> OTHER INFORMATION: deoxyuridine

<400> SEQUENCE: 15
ggauauuguc agucuuuagg uuuuu                                              25

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (10)..(10)
<223> OTHER INFORMATION: 5-fluoro-2'-deoxyuridine
<220> FEATURE:
<221> NAME/KEY: modified_base
<222> LOCATION: (16)..(16)
<223> OTHER INFORMATION: 5-fluoro-2'-deoxyuridine
<220> FEATURE:
```

```
<221> NAME/KEY: modified_base
<222> LOCATION: (18)..(18)
<223> OTHER INFORMATION: 5-fluoro-2'-deoxyuridine
<220> FEATURE:
<221> NAME/KEY: modified_base
<222> LOCATION: (21)..(25)
<223> OTHER INFORMATION: deoxyadenosine

<400> SEQUENCE: 16
ccuaaagacu gacaauaucc aaaaa                                           25

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (21)..(25)
<223> OTHER INFORMATION: deoxyuridine

<400> SEQUENCE: 17
ggauauuguc agucuuuagg uuuuu                                           25

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (16)..(16)
<223> OTHER INFORMATION: 5-fluoro-2'-deoxyuridine
<220> FEATURE:
<221> NAME/KEY: modified_base
<222> LOCATION: (18)..(18)
<223> OTHER INFORMATION: 5-fluoro-2'-deoxyuridine
<220> FEATURE:
<221> NAME/KEY: modified_base
<222> LOCATION: (21)..(25)
<223> OTHER INFORMATION: deoxyadenosine

<400> SEQUENCE: 18
ccuaaagacu gacaauaucc aaaaa                                           25

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (21)..(25)
<223> OTHER INFORMATION: deoxyuridine

<400> SEQUENCE: 19
ggauacugcc aaucucuagg uuuuu                                           25
```

```
<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (21)..(25)
<223> OTHER INFORMATION: deoxyadenosine

<400> SEQUENCE: 20
ccuagagauu ggcaguaucc aaaaa                                          25

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (21)..(25)
<223> OTHER INFORMATION: 5-fluoro-2'-deoxyuridine

<400> SEQUENCE: 21
ggauacugcc aaucucuagg uuuuu                                          25

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (21)..(25)
<223> OTHER INFORMATION: deoxyadenosine

<400> SEQUENCE: 22
ccuagagauu ggcaguaucc aaaaa                                          25

<210> SEQ ID NO 23
<211> LENGTH: 20
<212> TYPE: RNA
<213> ORGANISM: Homo sapiens

<400> SEQUENCE: 23
ggauauuguc agucuuuagg                                                20
```